(12) United States Patent
Zeilinger et al.

(10) Patent No.: US 9,557,262 B2
(45) Date of Patent: Jan. 31, 2017

(54) QUANTUM IMAGING WITH UNDETECTED PHOTONS

(71) Applicants: UNIVERSITY OF VIENNA, Vienna (AT); THE AUSTRIAN ACADEMY OF SCIENCES, Vienna (AT)

(72) Inventors: Anton Zeilinger, Vienna (AT); Sven Ramelow, Hainfeld (AT); Radek Lapkiewicz, Vienna (AT); Victoria Borish, Vienna (AT); Gabriela Barreto Lemos, Vienna (AT)

(73) Assignees: University of Vienna, Vienna (AT); The Austrian Academy of Sciences, Vienna (AT)

( * ) Notice: Subject to any disclaimer, the term of this patent is extended or adjusted under 35 U.S.C. 154(b) by 18 days.

(21) Appl. No.: 14/570,503

(22) Filed: Dec. 15, 2014

(65) Prior Publication Data

US 2015/0177128 A1 Jun. 25, 2015

(30) Foreign Application Priority Data

Dec. 19, 2013 (EP) .................................. 13198550

(51) Int. Cl.
*G01N 21/35* (2014.01)
*G01N 21/64* (2006.01)
(Continued)

(52) U.S. Cl.
CPC ............ *G01N 21/35* (2013.01); *G01N 21/636* (2013.01); *G01N 21/64* (2013.01); *G02F 1/39* (2013.01);
(Continued)

(58) Field of Classification Search
CPC ............ G01N 21/64; G01N 21/35; G02F 1/39
See application file for complete search history.

(56) References Cited

U.S. PATENT DOCUMENTS

| | | | | |
|---|---|---|---|---|
| 6,909,105 B1 * | 6/2005 | Heintzmann | .......... | G02B 21/00 250/550 |
| 7,274,440 B1 * | 9/2007 | Janik | ....................... | G01J 3/021 356/33 |
| 2005/0206904 A1 | 9/2005 | Zaugg | | |

FOREIGN PATENT DOCUMENTS

| | | |
|---|---|---|
| EP | 2058677 A1 | 5/2009 |
| NL | 1013929 C1 | 6/2001 |

OTHER PUBLICATIONS

ISA European Patent Office, International Search Report and Written Opinion Issued in Application No. PCT/EP2014/077755, Mar. 18, 2015, WIPO, 14 pages.

(Continued)

*Primary Examiner* — David Porta
*Assistant Examiner* — Mindy Vu
(74) *Attorney, Agent, or Firm* — Alleman Hall McCoy Russell & Tuttle LLP

(57) ABSTRACT

A method comprises: generating a first and a second correlated photon beam with wavelengths $\lambda_1$ and $\lambda_2$, respectively, wherein preferably $\lambda_1 \neq \lambda_2$; separating the first photon beam and the second photon beam; illuminating an object with the first photon beam; generating a third and a fourth correlated photon beam with wavelength $\lambda_1$ and wavelength $\lambda_2$, respectively; overlapping the first photon beam with the third photon beam such that photons of wavelength $\lambda_1$ in either photon beam are indistinguishable; overlapping the second photon beam with the fourth photon beam such that photons of wavelength $\lambda_2$ in either photon beam are indistinguishable; and using the overlapped photons of wavelength $\lambda_2$ for imaging and/or spectroscopy of the object such that the photons that illuminate the object are not detected.

20 Claims, 7 Drawing Sheets

(51) Int. Cl.
*G02F 1/39* (2006.01)
*G01N 21/63* (2006.01)
*G01N 21/47* (2006.01)

(52) U.S. Cl.
CPC ... *G01N 21/4795* (2013.01); *G01N 2201/0686* (2013.01); *G01N 2201/06113* (2013.01)

(56) References Cited

OTHER PUBLICATIONS

European Patent Office, European Search Report of EP13198550, Jun. 5, 2014, 8 pages.
Rogalski, Antoni. "Infrared detectors: an overview." Infrared Physics & Technology vol. 43, No. 3, Jun. 2002, pp. 187-210.
Vaughan, Peter M., and Rick Trebino, "Optical-parametric-amplification imaging of complex objects." Optics express vol. 19, No. 9, Apr. 22, 2011, pp. 8920-8929.
Van Voorthuysen, Eh du Marchie. "Quantum-Mechanical Indirect Measurements." Foundations of Physics Letters, vol. 10, No. 6, Dec. 1997, pp. 563-579.
Zou, X. Y et al., "Induced Coherence and Indistinguishability in Optical Interference", Physical review letters vol. 67, No. 3, Jul. 15, 1991, pp. 318.

\* cited by examiner

QUANTUM IMAGING WITH UNDETECTED PHOTONS

CROSS REFERENCE TO RELATED APPLICATIONS

The present application claims priority to European Patent Application No. 13198550.9, entitled "QUANTUM IMAGING WITH UNDETECTED PHOTONS," filed on Dec. 19, 2013, the entire contents of which are hereby incorporated by reference for all purposes.

FIELD OF THE INVENTION

The present invention relates to the field of imaging using correlated photons, in particular quantum imaging, and quantum spectroscopy.

BACKGROUND OF THE INVENTION

When a laser beam, called a pump laser beam, is transmitted through a non-linear crystal, due to the interaction between the laser light and the crystal, there exists some probability that a pump laser photon, with angular frequency $\omega_0$, is annihilated giving rise to a photon pair with different angular frequencies. The angular frequency $\omega$ is connected to the (ordinary) frequency $\nu$ by $\omega = 2\pi\nu$. In the following, the term frequency will also be used for the angular frequency $\omega$. Moreover, the angular frequency $\omega$ is connected to the corresponding wavelength $\lambda$ by $\lambda\omega = 2\pi c$, where c is the speed of light.

In accordance with the conservation of energy and momentum, the total energy and the total momentum of the two produced photons are equal to the energy and momentum, respectively, of the annihilated photon. The above described process of producing photon pairs using a non-linear medium is called spontaneous parametric down-conversion, SPDC. The relation between the frequencies of the photons as well as the wave vectors of the photons may be described as:

$\omega_0 = \omega_1 + \omega_2$ conservation of frequency, i.e. energy $k_0 = k_1 + k_2$ conservation of wave vector, i.e. momentum Here $\omega_0$ denotes the frequency of the pump photon, $\omega_2$ denotes the frequency of the so called signal photon and $\omega_1$ denotes the frequency of the so called idler photon. Due to energy conservation, the frequencies $\omega_2$ and $\omega_1$ are lower than the frequency $\omega_0$. Similarly, $k_0$ denotes the wave vector of the source photon, $k_2$ and $k_1$ denote the wave vector of the signal photon and idler photon, respectively. It should be noted that the two correlated photons may be spatially separated.

Photon pairs produced in non-linear media may be used for imaging. So-called quantum ghost imaging, cf. EP 2 058 677 A1, utilizes photon pairs produced by the interaction of a laser with a non-linear crystal, e.g. SPDC. One of the down-converted photon beams, also called photon fields or just fields, illuminates the object and is detected using a photon counter with no spatial resolution. This detection is used to herald a spatially resolving detector placed in the other one of the down-converted beams. Although only one of the down-converted fields illuminates the spatially resolving heralded detector, e.g., a triggered camera, the ghost image is seen in amplitude correlations between the twin beams. Hence the detection of both beams is always necessary. However, detecting the photons that illuminate the object may be problematic. For some applications, this requirement proves to be a major drawback of this imaging technique because there are not always detectors available at the wavelength necessary for the illumination of the object. The problem with using triggered cameras is that the detection of the signal photons on the camera must be triggered by the detection of its brother idler photon. The idler is usually detected with a photon counter and that signal is used to herald detection on the camera. Hence, signal and idler photons must both be detected within a small time window. Because of the relatively slow electronics, this implies that the signal be put in a long image preserving delay line, to give time for the idler to be detected and for this information to arrive at the camera at the same time as the signal photon arrives at the camera. This is a major drawback. This also implies that one needs excellent detectors for both of the photon wavelengths that are produced. However, MIR photon counters usually have high dark counts, such that these are not easy to use to trigger a camera.

Optical parametric amplification, OPA, cf. P. M. Vaughan and R. Trebino. "Optical-parametric-amplification imaging of complex objects." Optics Express, Vol. 19, Issue 9, pp 8920-8929 (2011), is another imaging technique. An object is illuminated with light from a pump laser and the light that illuminates the object is then sent through a non-linear crystal together with intense light from the pump laser. Photons generated by this process contain the image and are often at different wavelengths than the illumination pump laser. However this technique is rather complicated. In particular, the source has to be at the illumination wavelength the target should be illuminated with. This may be difficult to provide, especially when it comes to sources at non-visible wavelengths, of which only few are available. Moreover, this technique relies on a stimulated nonlinear process and therefore requires intense light beams. However, there may be many application areas such as imaging or studying fragile samples, e.g. biological samples, paintings etc. for which using intense light beams may not be needed or rather not wanted, since the high intensity would damage the sample.

One example may be organic compounds which exhibit specific absorption properties in the mid infrared, MIR. In medical imaging this could be relevant for cancer diagnostics, for example. MIR imaging may also be used in cultural heritage and paintings conservation. MIR imaging has additional applications in industrial imaging and security fields.

Imaging in the MIR regime may require sophisticated cameras. Such MIR cameras may be very demanding—a commonly used technical approach is based on cryogenic InSb semiconductor technology, cf. Rogalski, A. Infrared Physics & Technology 43 (2002) 187-210. MIR cameras are expensive and the InSb semiconductor technology inside needs to be cooled down to very low temperatures. However, these cameras still feature a lot of noise and often exhibit poor signal-to-noise ratios.

Other approaches to imaging may be based on the inverse process to down-conversion, namely nonlinear up-conversion. This technique requires relatively strong pump laser power, and a light source at the illumination wavelength. In up-conversion imaging, images are nonlinearly converted to a wavelength regime in which efficient and low-noise detectors may be available. Due to the requirement of strong pump lasers, in order to be efficient, using this technique for many applications is hampered if not impossible.

SUMMARY OF THE INVENTION

In view of the above, the present invention provides an alternative solution to imaging and/or spectroscopy with correlated photons in order to overcome the above-mentioned problems, e.g. to provide flexibility in choosing the wavelengths used both to illuminate the sample and to detect with a camera, thus providing an easy way for imaging and/or spectroscopy.

According the present invention, it is provided: A method comprising the steps of:
(i) generating one or more first, correlated, such as quantum entangled photon pairs, each pair having two photons with a wavelength $\lambda_1$ and a wavelength $\lambda_2$, respectively, thereby generating a first and a second photon beam with wavelength $\lambda_1$ and $\lambda_2$, respectively, wherein preferably $\lambda_1 \neq \lambda_2$;
(ii) separating the photons of wavelength $\lambda_1$ and the photons of wavelength $\lambda_2$;
(iii) illuminating an object with the photons having the wavelength $\lambda_1$;
(iv) generating one or more second, correlated, such as quantum entangled photon pairs, each pair consisting of two photons with a wavelength $\lambda_1'$ and a wavelength $\lambda_2'$, respectively, thereby generating a third and a fourth photon beam with wavelength $\lambda_1'$ and wavelength $\lambda_2'$, respectively wherein $\lambda_1'=\lambda_1$ and $\lambda_2'=\lambda_2$; and overlapping photons of wavelength $\lambda_1$ generated in step (i) with photons of wavelength $\lambda_1$ generated in step (iv), such that photons of wavelength $\lambda_1$ generated in either step are indistinguishable,
(v) overlapping photons of wavelength $\lambda_2$ generated in step (i) with photons of wavelength $\lambda_2$ generated in step (iv), such that photons of wavelength $\lambda_2$ generated in either step are indistinguishable;
(vi) using the overlapped photons of wavelength $\lambda_2$ for imaging and/or spectroscopy of the object; such that the photons that illuminate the object are not detected The correlation of photons within the method described above should be understood as spatial correlations for imaging, or as frequency correlations for spectroscopy. In particular, the correlations may be quantum entanglement, i.e. spatial or frequency quantum entanglement. It should be understood that the photon beams follow photon paths and that said terms may be used synonymously throughout this description.

In the following, the terms object and sample are used synonymously.

It is clear that in the above method the illuminating radiation may be used for imaging and/or for spectroscopy. The imaging/spectroscopy step of the method is largely independent from the illuminating step and the only governing principles are physical conservation laws such as the conservation of energy and momentum for the two photons of the correlated photon pair. Since the imaging/spectroscopy step is largely independent or in other words largely decoupled from the illumination step, this provides advantages for the choice of the imaging wavelength and the illumination wavelength, in particular for selecting different wavelengths. The illumination wavelength may be chosen such that the illuminated sample has some transparency or wavelength specific absorption for the illumination wavelength. The imaging/spectroscopy wavelength may be chosen such that the imaging equipment has sufficient efficiency, noise resilience, high spatial or temporal resolution, high frame-rate or high sensitivity at the imaging/spectroscopy wavelength.

It should be noted that at least one pair in step (i) should be produced or at least one pair in the step (iv) should be produced. At a given time, at the imaging/spectroscopy step (vi), one photon at a time having the imaging wavelength may arrive for imaging and the origin of said photon, i.e. whether it originated from step (i) or step (iv), is not known for the imaging/spectroscopy step.

It should be noted that in step (iv) the overlapping occurs during the generating of the one or more, second, correlated photon pairs.

It should be understood that in the separating step the two photon beams of the correlated photon pair are separated. Furthermore, due to the correlation of the photons, the method has intrinsically an efficiency of nearly 100% since the imaging photons may have the same intensity as the illumination photons. Furthermore, no extra light source need be provided at the illumination wavelength. It should be understood that the overlapping step ensures that the subsequent imaging/spectroscopy step has no information on the origin of the photons used for imaging/spectroscopy.

It should be understood that the overlapping step (iv) provides overlapping of the photons of wavelength $\lambda_1$ such that they are indistinguishable with regard to their source.

In the method, the one or more correlated photons of step (i) and step (iv) may be produced by a coherent light beam such as a laser beam, being incident on a non-linear medium such as a non-linear crystal.

A laser beam is a commonly available coherent light source. The laser beam used need not be pulsed and no optical resonators need to be used. Due to the high efficiency of basically 100%, the method will work down to the single photon or photon pair regime.

A non-linear medium may include a non-linear crystal. Examples for such crystals are (periodically poled) potassium titanyl phosphate, (pp)KTP, (periodically poled) Lithium-Niobate, (pp)LN, (periodically poled) stoichiometric lithium tantalate (pp)SLT, barium borate BBO, lithium triborate LBO, bismuth borate BiBO, and potassium dihydrogen phosphate KDP. It should be understood that this list is not exhaustive. The non-linear crystal may be periodically poled for enhanced efficiency. However having periodically poled crystals is not a prerequisite. In particular, bulk crystals may be used. It should be understood that other non-linear media, including higher-order non-linear media may be used.

In the method, the overlapping may be performed by means of a dichroic mirror or a beam splitter, such as a polarizing beam splitter, for example. The imaging in step (vi) may be performed by means of a CCD camera and/or a spectrometer.

A dichroic mirror may be a convenient means to be used for overlapping/aligning photon beams of different wavelengths. It should be understood that one or more dichroic mirrors may also be used for separating photon beams when needed. A standard charged coupled device, CCD, camera or CMOS camera or a spectrometer may be used for the imaging of the sample. Additionally, also phase properties of the sample/object and/or dispersion and/or thickness aspects of the sample may be imaged.

In the method, the one or more correlated photon pairs in step (i) may be generated by a first non-linear medium.

Light from a coherent light source incident on the first non-linear medium, e.g. the first non-linear crystal may produce the one or more correlated, in particular quantum entangled photon pairs.

In the method, the one or more correlated photon pairs in step (iv) may be generated by a second non-linear medium having the same physical properties as the first non-linear medium, and the second non-linear medium may be spatially separated from the first non-linear medium.

Light from the coherent light source incident on the first non-linear medium, e.g. the first non-linear crystal may produce the one or more second, correlated, in particular quantum entangled photon pair. It should be understood that the photon of wavelength $\lambda_1$ of the first photon beam is used for illuminating the sample. The light from the coherent light source may be split into two beams having the same wavelength of the source. One of the beams may be incident on the first non-linear medium. The other may be incident on the second non-linear medium, which is spatially separated from the first non-linear medium. The second non-linear medium should have the same physical and optical properties as the first non-linear medium. This has the advantage that a correlated photon pair generated by the second non-linear medium may have photons with wavelengths $\lambda_1'$ and $\lambda_2'$, respectively wherein $\lambda_1'=\lambda_1$ and $\lambda_2'=\lambda_2$. It should be understood that as for the first non-linear medium $\lambda_1 \neq \lambda_2$ may be preferable.

In the method, the one or more correlated photon pairs in step (iv) may be generated by the first non-linear medium.

In the method the photons of wavelength $\lambda_1$ may be reflected after illuminating the sample, such as to reverse their optical path.

As an alternative to having a second non-linear medium spatially separated from the first non-linear medium but the second non-linear medium having the same physical properties as the first non-linear medium, the first non-linear medium may be used to also generate the one or more second, correlated photon pairs. This allows for a very compact setup. This may include reflecting light of wavelength $\lambda_1$ after illuminating the sample/object. This may have the advantage of being applicable for optical coherence tomography applications. The sample may provide some reflectivity of incident light as well as some transmittance properties. Additionally, the photons of wavelength $\lambda_1$ may be reflected by a reflecting means such as to reverse their optical path.

In the method, the photon beams generated in step (i) and/or the photon beams generated in step (iv) may be collinearly generated.

In order to have a compact setup, it may be convenient to have the photon beam collinearly emitted. This may also make overlapping and alignment of the respective beams easier.

The invention further provides a system, the system comprising means for generating one or more first, correlated, such as quantum entangled, photon pairs, each pair consisting of two photons with a wavelength $\lambda_1$ and a wavelength $\lambda_2$, respectively, thereby generating a first and a second photon beam with wavelengths $\lambda_1$ and $\lambda_2$, respectively, wherein preferably $\lambda_1 \neq \lambda_2$; means for separating the photons of wavelength $\lambda_1$ and the photons of wavelength $\lambda_2$; means for illuminating an object with the photons having the wavelength $\lambda_1$; means for generating one or more second, correlated, such as quantum entangled, photon pairs, each pair consisting of two photons with a wavelength $\lambda_1'$ and a wavelength $\lambda_2'$, respectively, thereby generating a third and a fourth photon beam with wavelength $\lambda_1'$ and wavelength $\lambda_2'$, wherein $\lambda_1'=\lambda_1$ and $\lambda_2'=\lambda_2$; and for overlapping photons of wavelength $\lambda_1$ of the first photon pairs, having illuminated the object, with photons of wavelength $\lambda_1$ of the second photon pairs, such that overlapped photons of wavelength $\lambda_1$ are indistinguishable; and means for overlapping photons of wavelength $\lambda_2$ of the one or more first correlated photon pairs with photons of wavelength $\lambda_2'$ of the one or more second, correlated photon pairs, such that these overlapped photons of wavelength $\lambda_2$ are indistinguishable; and means for using the overlapped photons of wavelength $\lambda_2$ for imaging and/or spectroscopy of the object; such that the photons that illuminate the object are not detected.

The advantages of the above described system have already been discussed in view of the corresponding method. It should be noted that at least a pair consisting of two photons with a wavelength $\lambda_1'$ and a wavelength $\lambda_2'$, respectively, is produced at the means for generating one or more first, correlated, in particular quantum entangled photon pairs, or at least a pair consisting of two photons with a wavelength $\lambda_1'$ and a wavelength $\lambda_2'$, wherein $\lambda_1'=\lambda_1$ and $\lambda_2'=\lambda_2$; is produced at the means for generating one or more second, correlated, in particular quantum entangled photon pairs. At a given time, only one photon of the imaging/spectroscopy wavelength may arrive at the means for imaging/spectroscopy and the origin of said photon, i.e. whether it originated from the means for generating first photon pairs or means for generating second photon pairs, is not known for the imaging means.

The system may further comprise a coherent light source adapted to emit a coherent light beam such as a laser beam; wherein the means for generating the one or more first, correlated photon pairs may comprise a non-linear medium such as a non-linear crystal.

In the system, the means for overlapping photon beams may comprise a dichroic mirror; and the means for imaging/spectroscopy may comprise a CCD camera and/or a spectrometer.

In the system, the means for generating the one or more second, correlated photon pairs may comprise a second non-linear medium having the same physical and optical properties as the first non-linear medium, and the second non-linear medium, such a non-linear crystal, being spatially separated from the first non-linear medium.

In the system, the means for generating the one or more second, correlated photon pairs may be the same as the means for generating the one or more first, correlated photon pairs.

The system may further comprise a mirror adapted for reflecting the photons of wavelength $\lambda_1$ after illuminating the sample, such as to reverse their optical path.

In the system the first and second photon beams may be generated collinearly and/or the third and fourth photon beams may be generated collinearly.

The invention further provides use of a system as described above for imaging, in particular quantum imaging, and/or for performing spectroscopy, in particular quantum spectroscopy.

The invention further provides use of a system as described above for simultaneously performing imaging and spectroscopy.

Summarizing, the above method and the corresponding system for quantum imaging provide several advantages over prior art imaging concepts. In comparison with upconversion:
no strong laser is required to pump the non-linear crystal and therefore:
no cavities or pulsed lasers are required;

the phase profile imparted by the sample may be directly imaged;

dispersion properties of an object/sample may be directly measured;

thickness aspects of a sample can be directly measured;

no additional light sources are required at the wavelength used for illuminating the object; and the method provides intrinsically an efficiency of nearly 100%, thus the image beam has the same intensity as the illumination beam.

In comparison with ghost imaging:

no coincidence detection is required;

the illuminating radiation need not be detected, and therefore standard CCD, CMOS cameras, and spectrometers may be used;

transient phenomena may be conveniently observed;

the phase profile imparted by the sample may be directly recovered;

dispersion properties of a sample may be directly measured; and thickness properties of a sample may be directly measured.

In comparison with OPA:

OPA requires a coherent light source at the illumination wavelength whereas the present method does not require a coherent light source at the illumination wavelength which is an advantage since sources at non-visible wavelengths may be difficult to obtain.

OPA relies on a stimulated nonlinear process and thus requires intense light beams whereas the present method does not require stimulation and may therefore work at low intensities. In other words the sample/object to be imaged need not be illuminated by direct laser light so that sensitive samples may be imaged without damage.

Thus, the invention may be important for applications in several important areas, e.g., the invention may facilitate imaging normally carried out using special MIR cameras in the fields of atmospheric chemistry, diagnostics, and others i.e. detection of atmospheric gases, toxic agents, explosives, pollutants, components of human breath, free-space communication, non-destructive materials testing, biological imaging, OCT, especially ophthalmology, microscopy, national security, surveillance etc.

In other words, the present invention provides that an object/sample may be irradiated with photons of a suitable wavelength for illumination, whereas the imaging and/or spectroscopy may be performed on other photons with whatever other suitable means. The invention thus provides the flexibility to use convenient radiation sources and detectors, and to perform imaging or spectroscopy using wavelengths that are difficult or expensive to detect, for example, but not exclusively, in the mid infrared or the far infrared for astronomical imaging. The imaging means and/or spectroscopy means may be positioned spatially apart from the illumination means; this may permit to avoid walls or other obstructions/obstacles. This may also apply for fog and/or cloud cover, e.g. for applications for Intelligence-Surveillance-Reconnaissance ISR.

The above and other aspects, features and advantages of the present invention will become more apparent from the following detailed description when taken in conjunction with the accompanying drawings.

DETAILED DESCRIPTION

Figure 1:
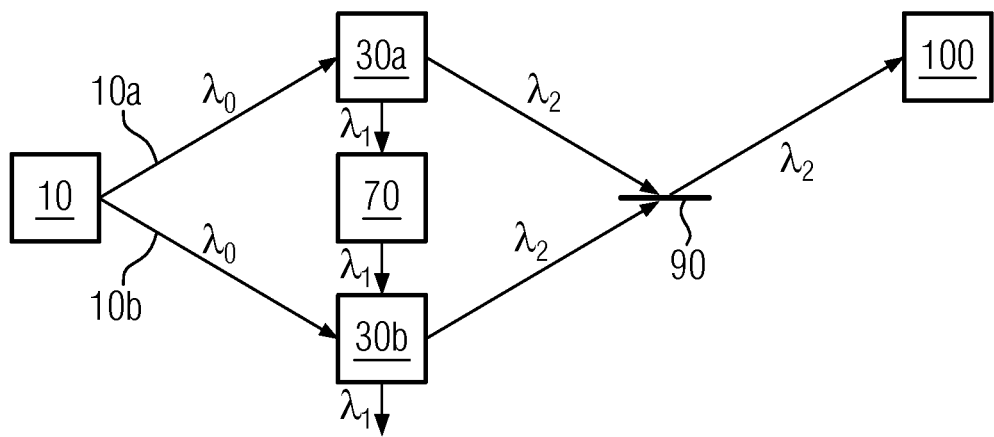
FIG. 1 shows a system according to a first embodiment of the present invention.

FIG. 1 shows a first embodiment according to the present invention comprising a basic interferometric setup. The setup is used for imaging the sample/object 70 shown in the middle of FIG. 1.

In FIG. 1, a coherent light source, such as a coherent laser 10 is used for providing a source beam, which is often also called pump beam. The coherent laser source 10 provides two beams 10a and 10b of light both having a source/pump wavelength $\lambda_0$. In principle, the coherent light source 10 may include an integrated beam splitter (not shown). The two light beams 10a and 10b, each having the source/pump wavelength $\lambda_0$, typically are emitted from the source 10 at some angle. FIG. 1 further depicts each of the two light beams 10a and 10b being incident on two non-linear media, such as non-linear crystals, 30a and 30b. That is, beam 10a is incident on the non-linear medium 30a in the upper half of the setup, which may be called a first non-linear medium, whereas beam 10b is incident on the second non-linear medium 30b in the lower half of the setup. The first and the second non-linear media 30a and 30b have the same physical and optical properties.

Each pump photon of the beams 10a and 10b may produce a photon pair at either non-linear medium 30a or 30b. Photon pairs produced at 30a and 30b may be produced via SPDC, for example. These photon pairs have wavelengths $\lambda_1$ and $\lambda_2$ respectively. The photons with wavelength $\lambda_1$ originating from non-linear medium 30a are used to illuminate the sample/object 70, which is to be imaged. After having illuminated the sample 70, the photons with wavelength $\lambda_1$ are incident onto the second non-linear medium 30b. Pump photon beam 10b is incident on non-linear medium 30b. The second non-linear medium, i.e. crystal, 30b also produces photon pairs consisting of two photons with wavelengths $\lambda_1'$ and $\lambda_2'$, respectively; wherein $\lambda_1'=\lambda_1$ and $\lambda_2'=\lambda_2$. After having illuminated the sample 70 the photons with wavelength $\lambda_1$ are incident onto the second non-linear medium 30b, where the photons with wavelength $\lambda_1$ produced in non-linear medium 30b are overlapped and aligned such that photons with wavelength $\lambda_1$ produced in either media 30a or 30b are indistinguishable. Using a combining means 90, the beams of photons having wavelength $\lambda_2$ coming from the first medium 30a are combined, i.e. overlapped, with photons having a wavelength $\lambda_2$ coming from the second medium 30b. This may be achieved by aligning the two beams or using a device such as a beam splitter, for example a polarized beam splitter. Thus, it is not possible to identify from which of the two media, 30a and 30b, the photon came, thereby rendering the photons with wavelength $\lambda_2$ indistinguishable. The coherence of the photons with wavelength $\lambda_2$ is a result of the indistinguishability of the corresponding twin photons with frequency $\lambda_1$. In other words, this may be viewed as feeding photons coming from the first non-linear medium 30a and having illuminated the object 70 with wavelength $\lambda_1$ into the second nonlinear crystal 30b and thereby making photons with wavelength $\lambda_1$ and $\lambda_1'=\lambda_1$ indistinguishable with respect to their source of origin. Then, the imaging of the sample 70 is performed with the overlapped photons of wavelength $\lambda_2$ using an imaging device 100, such as a charged coupled device (CCD) camera. The wavelength $\lambda_2$ may be separately chosen from the wavelength $\lambda_1$, in particular according to the needs of the imaging device/imaging means—whereas the wavelength $\lambda_1$ may be chosen according to the specific parameters of the object to be imaged. For spectroscopy, the device 100 may be replaced or complemented by a spectrometer for performing spectroscopy, in particular quantum spectroscopy. This may utilize frequency correlations of the photon pairs.

Figure 2:
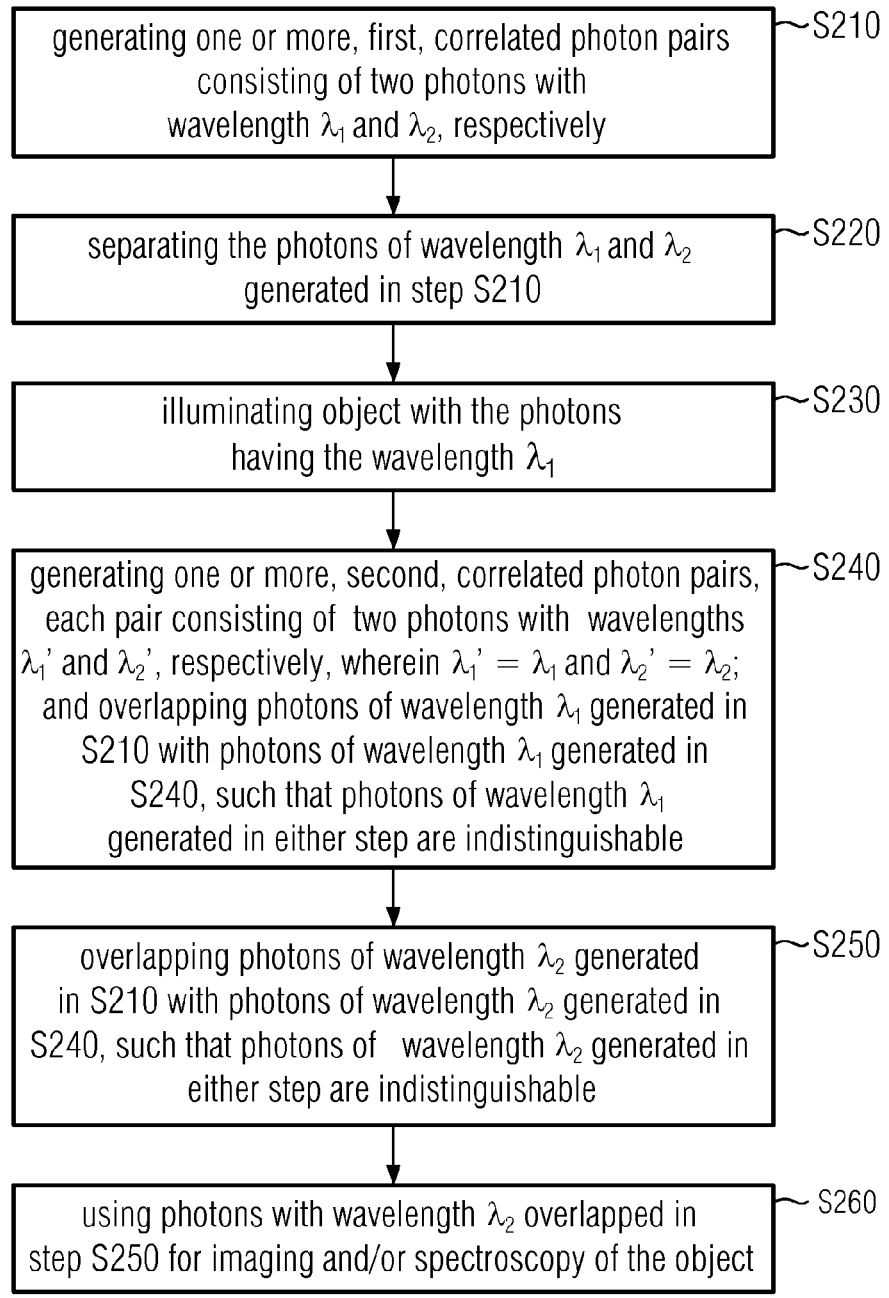
FIG. 2 shows a method according to the present invention.

FIG. 2 shows the corresponding method according to the present invention. In FIG. 2, step S210 indicates generating first, correlated, for example entangled, photon pairs with photons with wavelength $\lambda_1$ and $\lambda_2$, respectively. That is, after this generating step two photon beams have been generated, one with photons with wavelength $\lambda_1$, the other with photons with wavelength $\lambda_2$. Step S220 is the separating step of the photons of wavelength $\lambda_1$ and $\lambda_2$, which were generated in step S210. Thereafter the two photon beams are separated. It should be noted that this may also occur at the same time the photon pair is generated, such as in a non-collinear SPDC. In step S230 the object is illuminated with the photons having the wavelength $\lambda_1$. In step S240 a second, correlated, for example entangled photon pair is generated, having two photons with wavelength $\lambda_1'$ and $\lambda_2'$, respectively; wherein $\lambda_1'=\lambda_1$ and $\lambda_2'=\lambda_2$, i.e. the second correlated photon pair has photons with the same wavelengths as the first correlated photon pair; and the photons of wavelength $\lambda_1$ generated in S210, which thereafter have illuminated the object in step 230 are overlapped with photons of wavelength $\lambda_1$ generated in S240, during their generation in S240 such that photons of wavelength $\lambda_1$ generated in either step S210 or S240 are indistinguishable. In step S250 the photons of wavelength $\lambda_2$ generated in S210 are overlapped, e.g. at a beam splitter, with the photons of wavelength $\lambda_2$ generated in step S240, such that photons of wavelength $\lambda_2$ generated in either step are indistinguishable. In step S260 the image or spectrum of the object/sample is obtained using the photons with wavelength $\lambda_2$, which were overlapped in step S250 and whose source of origin is unknown due to the overlapping.

Figure 3:
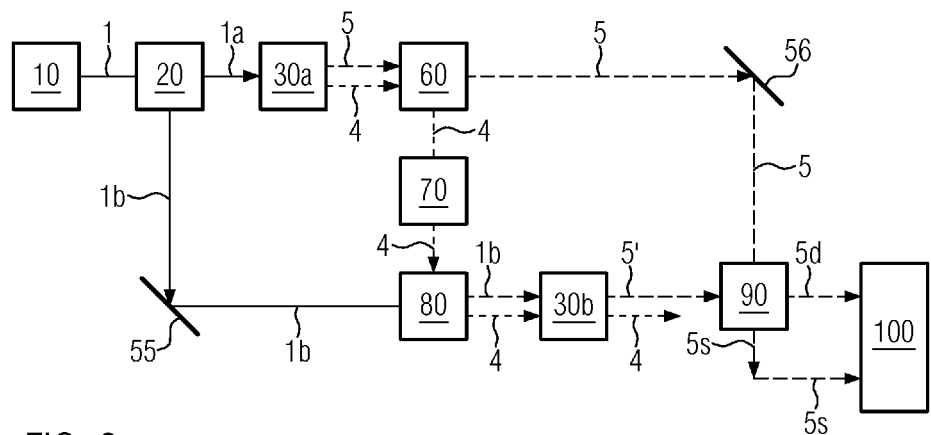
FIG. 3 shows a system according to a second embodiment of the present invention.

FIG. 3 shows a system according to another embodiment of the present invention. Similar elements of FIGS. 1 and 3 are denoted by similar reference signs. The system shown in FIG. 3 is similar to the embodiment shown in FIG. 1, with the difference that the photon pairs are produced collinearly with the pump laser. In an interferometric setup, the sample/object 70 is placed in between the two non-linear media, e.g. non-linear crystals 30a and 30b. The photons may be produced via the non-linear media 30a and 30b with corre-lations, such as transverse spatial or frequency entanglement. A coherent light source 10 produces a coherent light beam, such as a laser beam, denoted by 1, having the wavelength $\lambda_0$. The light beam 1 is incident on a beam splitter 20. The beam splitter 20 may be a polarizing beam splitter (PBS), a tunable beam splitter, or a normal beam splitter. The beam splitter will ensure that the source beam is split into two beams 1a and 1b, both having the wavelength $\lambda_0$. The beam 1a is incident onto the first non-linear medium 30a.

The first non-linear medium 30a may produce a correlated photon pair, i.e. two beams 5 and 4 of correlated photons having wavelengths $\lambda_2$ for beam 5 and $\lambda_1$ for beam 4. The production in 30a may occur via SPDC. In this embodiment, the two photon beams of entangled photons may exit the non-linear medium collinearly. Substantially collinear photon beams will be more convenient for imaging. The overlapping and/or aligning may be less complex, i.e. may take less time, and wavelength tunability may be improved. It should be understood, however, that also a non-collinear realization may be possible. Both beams enter a separating means 60 such as a dichroic mirror in order to separate the two beams, i.e. beam 5 having photons with wavelength $\lambda_2$ from beam 4 having photons with wavelength $\lambda_1$. It should be pointed out that beam 5 may also be called the signal beam with signal photons whereas beam 4 may be called the idler beam with idler photons. The beam 4 having the idler photons of wavelength $\lambda_1$ illuminates the sample/object 70; thereby the object is traversed to some degree by the photons of beam 4. After illuminating the sample 70, the photons of beam 4 are incident onto another combination/separation means 80 such as another dichroic mirror. The means, e.g. dichroic mirror 80, also receives the photon beam 1b having wavelength $\lambda_0$. For a collinear realization, element 80 may combine, i.e. align, photon beam 1 and the photon beam 4, after the photon beam 4 has illuminated the sample 70.

The aligned paths having photons with wavelengths $\lambda_0$ and $\lambda_1$ exiting element 80 is incident on the second non-linear medium 30b. The second non-linear medium 30b, having the same physical properties as the first non-linear medium 30a, is spatially separated from 30a. As with the first non-linear medium 30a, the second non-linear medium 30b generates correlated, for example quantum entangled, photon beams from the incident source photon beam having wavelength $\lambda_0$. The quantum entangled photon beams are denoted 5' and 4, wherein the beam 5' corresponds to photons of wavelength $\lambda_2$, and the photon beam 4 exiting 30b corresponds to photons of wavelength $\lambda_1$, which, due to overlapping, are indistinguishable from beam 4 photons originating in 30a. It should be understood that the beam 4 exiting the non-linear medium 30b has photons of the same wavelength $\lambda_1$ as the beam 4 incident on element 30b. These beams of wavelength $\lambda_1$ are in that respect indistinguishable. The beam of photons of wavelength $\lambda_1$ need not be further considered after element 30b.

Figure 4:
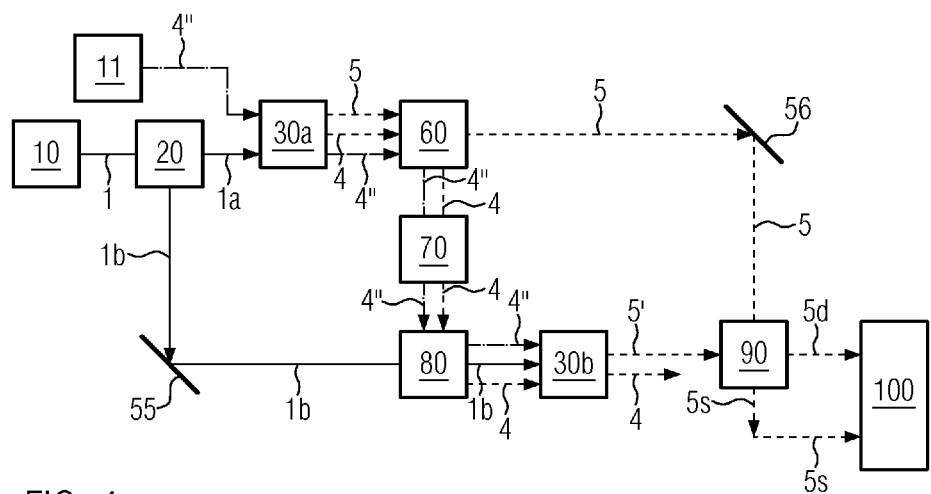
FIG. 4 shows a system showing a modification of the second embodiment of the present invention.

The beam 5' of photons with wavelength $\lambda_2$ in FIG. 3 is incident on a combining means 90, which may be a device such as a regular beam splitter, which overlaps the beams 5 and 5'. It should be noted that FIG. 4 shows a largely symmetric setup of the elements 20, 30a, 60, 90 using source beam 1a and signal photons 5 with the elements 20, 80, 30b, 90 with the source beam 1b and signal photons 5', wherein element 90 provides that photons of beam 5 and 5' are rendered indistinguishable, e.g., by overlapping of these beams. The photon beam exiting element 90 is then again denoted 5. The imaging using the photon beam 5 after the overlapping step is performed with imaging means 100 in FIG. 3. This imaging means may be, for example, a CCD camera, a CMOS camera, or a spectrometer. Both phase and amplitude of the sample 70 may be retrieved. It should be noted, again, that both the source and the imaging/spectroscopy photons may be differently chosen from the photons illuminating the object 70. This implies that the imaging may be performed at a wavelength for which one needs neither a specific source wavelength nor a specific illumination wavelength. The choice of wavelength for imaging thus is largely decoupled from the source wavelength.

Selecting different pairs of non-linear media 30a and 30b, e.g., different pairs of non-linear crystals may provide different combinations of wavelengths. Therefore, these wavelengths, and thus the corresponding frequencies, for the twin photons provide much flexibility in choosing the wavelengths used both to illuminate the sample and to image with a camera or detect with a spectrometer. Since both phase and amplitude information is shared between the correlated photons, this system may be used with phase and/or amplitude samples. The method as shown in FIG. 3 may use photons pairs produced by SPDC. The method does not require coincidence measurements.

One or more mirrors may be included to direct photons towards an appropriate means. For example, as depicted in FIG. 3, mirror 55 may reflect beam 1b towards the non-linear medium 80, while mirror 56 may reflect beam 5 toward the combining means 90.

A specific example fitting to the embodiment of FIG. 3 will be discussed below.

FIG. 4 shows a slightly modified embodiment, which is based on the embodiment shown in FIG. 3. All elements of FIG. 3 are also present in FIG. 4 and are denoted with the same reference signs, and will not again be explained here. FIG. 4 also shows an additional coherent light source, i.e., an additional laser 11. Whereas the above embodiment discussed for FIG. 3 will be well suitable even for very low light intensities, some applications may require higher power. In case higher laser power, i.e. high light intensities, should be required, the additional laser 11 having a laser beam of wavelength $\lambda_1$ may be added to the setup shown in FIG. 3. Thus, the number of photons traversing the object/sample may be increased. The additional laser 11 may produce a laser beam 4" having wavelength $\lambda_1$, which would be aligned with the path of the photon having wavelength $\lambda_1$ produced in the non-linear medium 30a, e.g. the first crystal. This beam would then also traverse the second non-linear medium 30b, e.g. the second crystal, as is shown in FIG. 4. This additional laser 11 would thus shine through both nonlinear media, 30a and 30b, and the sample 70, respectively. This corresponds to stimulated parametric down-conversion.

Figure 5:
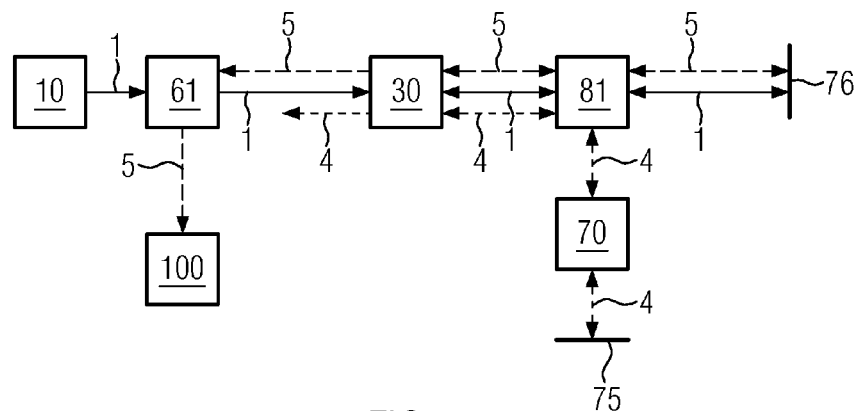
FIG. 5 shows a system showing another embodiment of the present invention.

A further embodiment is shown in FIG. 5. Similar to the embodiment shown in FIG. 3, a coherent light source 10 such as a pump laser may be used in another interferometric setup. The pump laser produces a source photon beam with photons of wavelength $\lambda_0$. In the embodiment shown in FIG. 5, the source photons pass element 61 largely without change. The photons originating from the pump laser then pass through a non-linear medium, such as a non-linear crystal, 30. The non-linear medium may be similar to the non-linear media in the previous examples, i.e. similar to elements 30a and 30b shown in FIGS. 1, 2, and 3. Similar to the other embodiments, correlated twin photons with wavelengths $\lambda_1$ and $\lambda_2$ are produced in the non-linear medium 30. That is, just as in the other embodiments, a signal photon beam 5 having photons with wavelength $\lambda_2$ as well as an idler photon beam 4 having photons with wavelength $\lambda_1$ are produced by the non-linear medium 30. The photon beams 4 and 5 may exit the non-linear medium collinearly. They are incident on element 81, which represents a separation and combination means, e.g. a dichroic mirror. Element 81 is suitable to separate photon beam 4 from photon beam 5. Photon beam 5 remains aligned with photon beam 1, which also passes through element 81. Photon beams 5 and 1 exit element 81 preferably collinearly and are reflected by mirror 76, which represents a mirror capable of reflecting at least photons of both wavelengths $\lambda_2$ and $\lambda_0$. Alternatively, two different mirrors may be used to reflect these photons back onto element 81.

The idler photon beam 4 having photons with wavelength $\lambda_2$ and separated from the other beams 1 and 5 exits element 81 and is incident on the object/sample 70. After illuminating the sample the photon beam 4 is reflected back onto element 81 by means of a mirror 75 behind the sample 70. If the samples is reflective or provides at least some degree of reflectivity it may not be necessary to provide mirror 75.

Element 81, for example a dichroic mirror, re-combines photon beams 1, 4 and 5. It should be again pointed out that photon beam 4 has illuminated the sample 70. The photon beams 1, 4 and 5 are again incident onto non-linear medium 30. The interaction of beam 1 with element 30 may create a second, correlated photon pair with wavelengths $\lambda_2$ and $\lambda_1$ which are indistinguishable from incident photons of photon beam 5 and 4, respectively, since the incident and the outgoing beams are kept aligned. Photon beams 5 and 4 produced in element 30 are then incident onto element 61 which then may separate these beams. The photons of beam 5, i.e. the signal photons that did not go through element 70 may then be incident onto imaging device 100, which may be a CCD camera, a spectrometer, or any other detector.

This embodiment may be used for optical coherence tomography, OCT, a technique used extensively in biology imaging and/or in medicine. OCT in the frequency domain may be realized using a spectrometer as a detector and using a sample 70 comprising a stack of partially reflective layers with respect to the incident wavelength $\lambda_1$. As with the other embodiments, the sample is illuminated with photons of wavelength $\lambda_1$ whereas the imaging is performed with photons of wavelength $\lambda_2$. This embodiment thus may provide broadband as well as tunable light which may be important for OCT applications, e.g., non-destructive materials testing, biological imaging, and imaging in ophthalmology.

As a further modification, chirped periodically-poled crystals may be used to maximize the bandwidth. Here also the main advantage would be the flexibility in the choice of the wavelength in that the wavelength that probes the sample may be different from the wavelength that is imaged by the spectrometer.

It should be noted that in all of the above-described embodiments, additional lenses may be used for further enhancing the mapping of the optical systems such that at a given point, the idler photons created from both non-linear media are substantially identical in frequency, spatial distribution and phase distribution. However, use of such lenses is not a prerequisite for these embodiments.

Interference in the frequency domain may also be used for measurements of the refractive index as a function of wavelength, i.e., dispersion. The same may be used to determine the thickness or length of the sample if the refractive index is known. Indeed, the method and system according to the present invention may be used in dispersion measurements, interferometry, spectroscopy, microscopy, and imaging whenever wavelength flexibility is required.

EXAMPLES

The following should provide proof of principle results, using the above-described embodiments.

Figure 6:
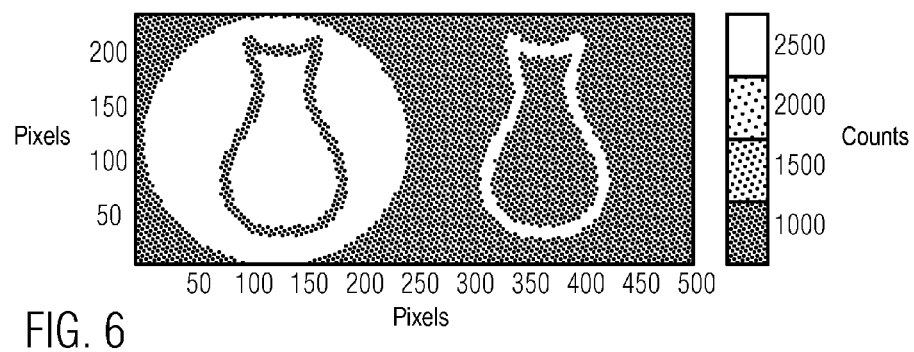
FIG. 6 shows an example showing the result of imaging a sample, achieved according to an embodiment of the invention.

In FIG. 6 a first example is shown. For this example, two periodically poled potassium titanyl phosphate, ppKTP, crystals are used as non-linear media. It should be noted that bulk crystals could be used as well. The sample is a silicon sample. The sample has a figure, i.e., a symbolic cat-like outline, etched on the sample. The source beam is a 532 nm pump laser. The sample is then illuminated with 1550 nm photons. This may be regarded as a telecom wavelength. Cameras available at this wavelength are usually very expensive and exhibit lower performance than in the visible light spectrum. Moreover, such cameras may be subject to severe export restrictions. The image, however, is generated by using 810 nm photons impinging on the image generator. These photons with a wavelength of 810 nm do not interact with the sample.

It should be noted that silicon is basically opaque for illumination at 810 nm, wherein it is highly transparent at 1550 nm, and thus could not be imaged directly with 810 nm light.

The beam splitter used in this example is a 50:50 beam splitter with two outputs so as to provide additionally or alternatively a sum of the two input signals and/or a difference of the two input signals. The detection of the 810 nm photons may be realized simultaneously in both outputs of the beam splitter. The imaging device may be a suitable imaging device, in this example an Electron Multiplying Charge Coupled Device, EMCCD, camera. Such a camera has single photon sensitivity for photons impinging on the camera at 810 nm, but has a negligible response at 1550 nm. Thus, this camera is effectively blind for 1550 nm photons. For the example, a combination of spectral filters was used before said camera. These have the effect to further reduce any contributions from background light of either source photons or idler photons such that neither 1550 nm photons nor 532 nm source photons would reach the camera. It should be understood, however, that the use of these filters is optional. In this example a spectral filter defines a 3 nm bandwidth for the 810 nm single photons. No heralding is used.

As results, FIG. 6 shows the interference image on the left side and the complementary interference image on the right side of FIG. 6. FIG. 6 shows the astounding result that the outline etched on the sample is clearly visible using the 810 nm photons even though the sample has been illuminated only with 1550 nm photons and moreover the sample is opaque for 810 nm photons. Due to spatial correlation between the signal and idler photons, interference is only observed in the region of the 810 nm output beams for which their corresponding 1550 nm photons were illuminating the sample. The 1550 nm photons were not detected.

Figure 7:
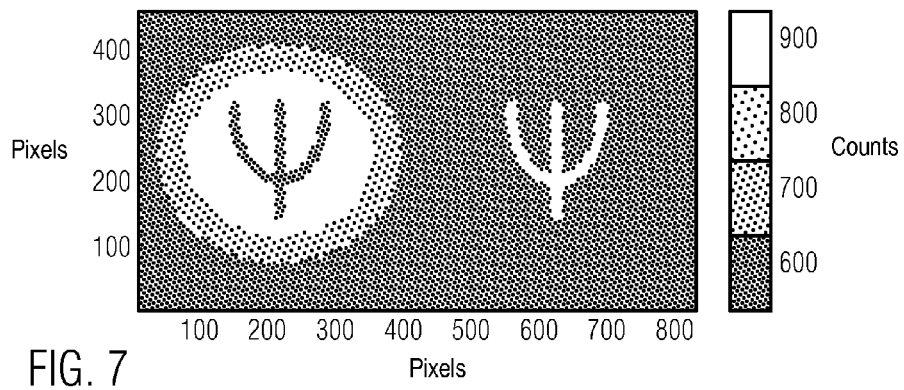
FIG. 7 shows another example showing the result of imaging a different sample, achieved according to an embodiment of the invention.

FIG. 7, shows another proof of principle result, using the above-described embodiments. The non-linear medium and the imaging device are the same as for the previous example. In this example, a glass sample was used. Said sample has a Greek capital letter Ψ etched on it. The sample was illuminated with photons of wavelength 1515 nm. The imaging was performed using the same CCD camera as, for the example, shown in FIG. 6, at 820 nm. As results, similar to in FIG. 6, the interference image is shown on the left side of FIG. 7 and the complementary interference image is shown on the right side of FIG. 7. FIG. 7 shows that the Greek capital letter Ψ etched on the sample is clearly visible using the 820 nm photons even though the sample has been illuminated only with 1515 nm photons that were not detected at all.

In the following, three more Figures are shown as a proof of principle of the method described above.

Figure 8:
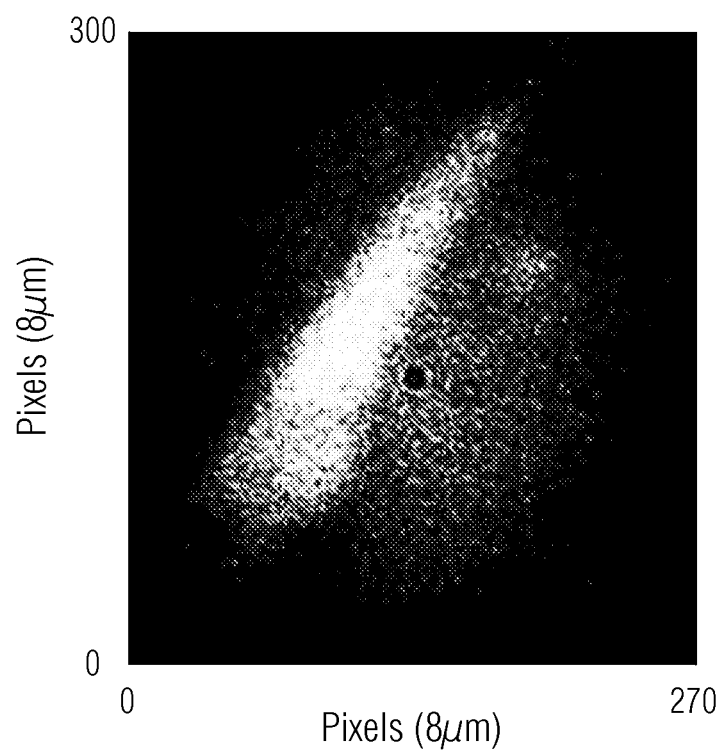
FIG. 8 shows a further example of a still image from a video of a live Casper zebrafish larva using basically the same setup as was used for examples shown in FIGS. 6 and 7.

FIG. 8 shows a further example of a still image from a video of a live Casper zebrafish larva using basically the same setup as was used for examples shown in FIGS. 6 and 7, respectively. The zebrafish was imbedded in an immobilising gel placed in a small chamber. The fish is illuminated with single photons having a wavelength of 1550 nm. The image shown in FIG. 8, however, is obtained by detecting only photons of a wavelength of 810 nm. Because it is possible to perform real-time imaging, it is even possible to film the fish's movement.

Figure 9:
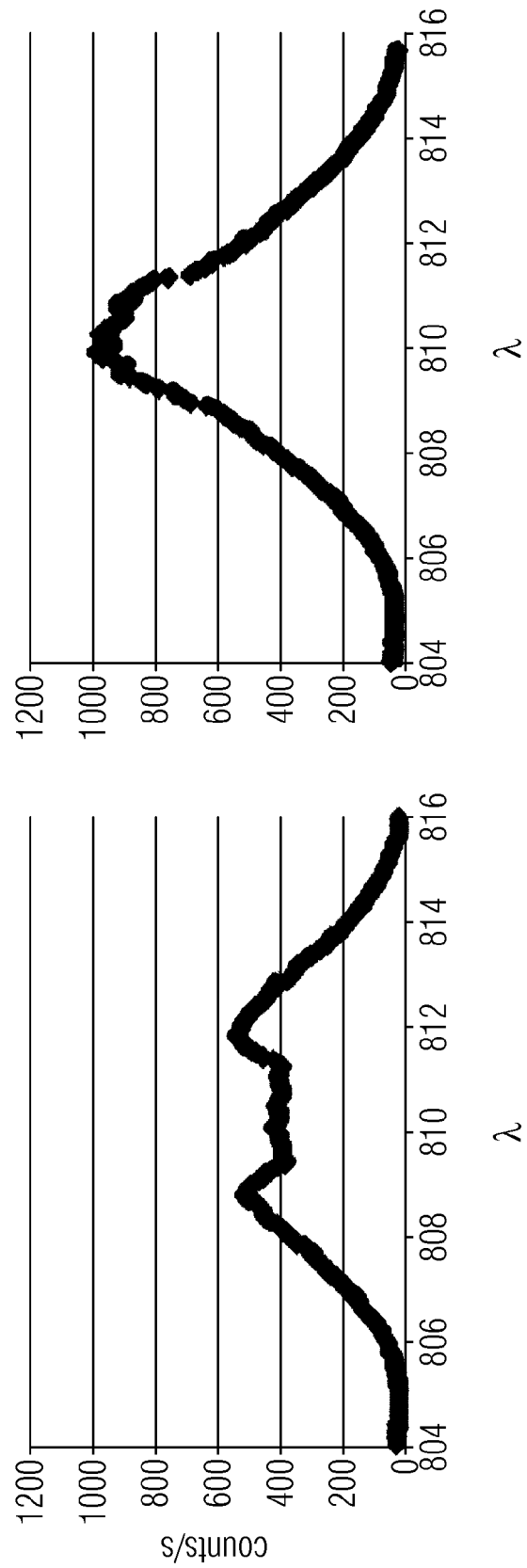
FIG. 9 shows a further example of spectral fringes which are seen when an object with a certain depth and index of refraction is inserted in the same setup as was used for obtaining the images of FIGS. 6 and 7.

FIG. 9 shows a further example of spectral fringes which are seen when an object with a certain depth and index of refraction is inserted in the same setup as was used for obtaining the images of FIGS. 6 and 7, respectively. The object may be inserted in any of the two "arms" of the interferometer setup. The number of fringes is proportional to the index of refraction at the illumination wavelength times the thickness of the sample. Here instead of a camera, a spectrometer was used to detect the 810 nm photons. This type of measurement may further refer to measuring the correlation of polarisation of photons, as may be highly correlated with regard to their polarisation. Using a birefringent object, stress birefringence imaging may be observed. Both diagrams in FIG. 9 display an interference pattern. The difference between the diagram on the right side of FIG. 9 and on the left side of FIG. 9 is the number of rings of the interference pattern. This number is proportional to the index of refraction, at the incident wavelength of the photons, of the medium.

Generalising the example as depicted in FIG. 9, the system of the invention also provides the possibility to use the polarisation degree of freedom of the photons and then to image spatially dependent birefringence coefficients of materials/objects under study, as it is shown by using the embodiments described above. That is, the object comprises a birefringent material, in particular exhibiting birefringence when the object is put under stress. The stress may be mechanical stress. A birefringent material is a material for which the optical refractive index depends on polarization and propagation direction of the light which illuminates the material. Normal materials such as isotropic solids do not exhibit birefringence. However, when they are under mechanical stress, birefringence may result. The stress may be applied externally or is "frozen in". One example may be a birefringent plastic material which is cooled after it is manufactured by injection moulding. If such a sample is placed between two crossed polarisers, color patterns may be observed, because polarization of a light ray is rotated after passing through a birefingent material and the amount of rotation is dependent on wavelength. This has important applications such as applying stress birefringence imaging which is used for birefringence imaging in biological applications.

Figure 10:
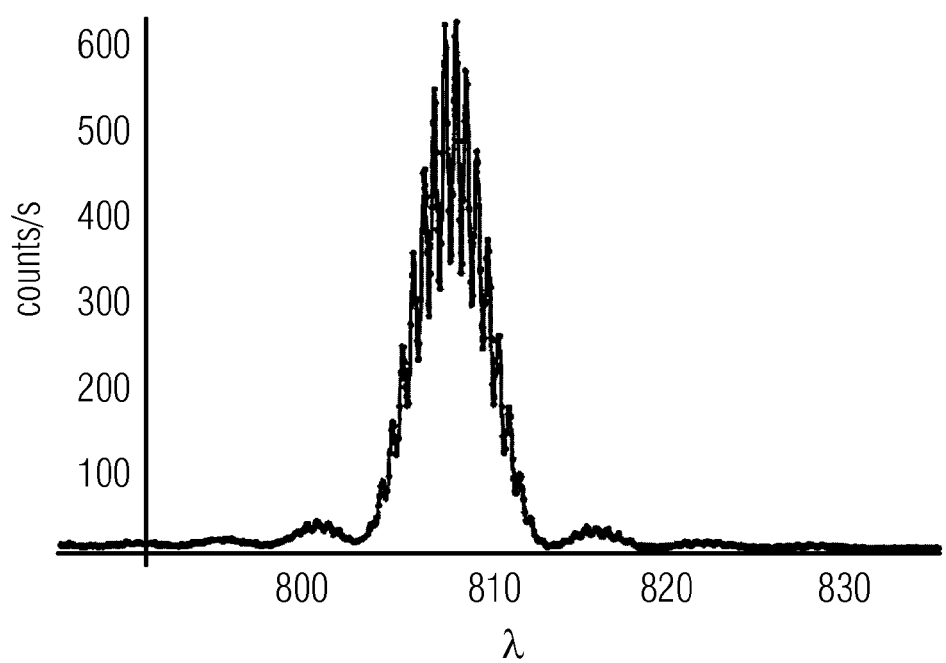
FIG. 10 shows a further example using the same setup as was used for obtaining FIGS. 6 and 7, respectively, inserting a 3 nm FWHM bandpass filter.

FIG. 10 shows a further example using the same setup as was used for obtaining FIGS. 6 and 7, respectively. A 3 nm FWHM, Full width at half maximum, bandpass filter centred at a wavelength of 1550 nm was put into the path of the photons of 1550 nm of the setup. This means that only light with wavelength 1550 nm±1.5 nm passes through this bandpass filter. Due to spectral correlations between the two down-converted photons created at either crystal, there is only interference in the corresponding wavelengths of the imaged photons of wavelength 810 nm. Thus the peak in FIG. 10 is centred at 810 nm. The spectral regions outside the peak region correspond to short-wavelength infrared, SWIR, photons which are absorbed by the bandpass filter, showing no interference.

Summarizing FIGS. 8 through 10, an advantage of this invention is that one may not only image at a wavelength in which single-photon sensitive cameras are available, but one may also choose the cameras that are best suited for the imaging demand of each experiment, as it is substantiated by the above images. For images that require good resolution one may use cameras with the best resolution on the market, and if contrast is the main issue then one may use cameras with a large dynamical range, e.g. silicon based cameras. When using a stimulated laser in the setup to induce emission in the second crystal, the object may be placed in the stimulated beam, before it is fed into the second crystal. In this case the two idler, i.e. infrared, paths coming from either crystal do not have to be aligned, which makes the setup easier to align and more robust. Also the polarisation degree of freedom of the photons may be used and one may image spatially dependent birefringence coefficient of materials. A birefringent material is one for which the optical refractive index depends on polarization and propagation direction of the light illuminates the material. The imaging method may be applied for stress birefringence imaging which may be used for birefringence imaging in biological applications.

The invention claimed is:

1. A method, comprising:
generating one or more first correlated photon pairs, each pair comprising two correlated photons with a wavelength $\lambda_1$ and a wavelength $\lambda_2$, respectively, thereby generating a first and a second photon beam with wavelengths $\lambda_1$ and $\lambda_2$, respectively, wherein $\lambda_1$ does not equal $\lambda_2$;
separating the first photon beam and the second photon beam;
illuminating an object with the first photon beam;
generating one or more second correlated photon pairs, each pair comprising two correlated photons with a wavelength $\lambda_1'$ and a wavelength $\lambda_2'$, respectively, thereby generating a third and a fourth photon beam with wavelength $\lambda_1'$ and wavelength $\lambda_2'$, respectively, wherein $\lambda_1'$ equals $\lambda_1$ and $\lambda_2'$ equals $\lambda_2$;
overlapping the first photon beam with the third photon beam such that the photons of wavelength $\lambda_1$ in either photon beam are indistinguishable;
overlapping the second photon beam with the fourth photon beam such that the photons of wavelength $\lambda_2$ in either photon beam are indistinguishable; and
imaging the object using the overlapped photons of wavelength $\lambda_2$ without detecting the overlapped photons of wavelength $\lambda_1$.

2. The method of claim 1, wherein the overlapping is performed by means of a dichroic mirror, and wherein the imaging is performed by means of a CCD camera.

3. The method of claim 1, wherein the one or more first correlated photon pairs are generated by a first non-linear medium.

4. The method of claim 3, wherein the one or more second correlated photon pairs are generated by a second non-linear medium having the same physical and optical properties as the first non-linear medium, and wherein the second non-linear medium is spatially separated from the first non-linear medium.

5. The method of claim 1, further comprising reflecting the photons of wavelength $\lambda_1$ to reverse their optical path after illuminating the object.

6. The method of claim 1, wherein the first and second photon beams are collinearly generated, and the third and fourth photon beams are collinearly generated.

7. The method of claim 1, wherein each of the generated photon pairs bears spatial and/or spectral correlation.

8. The method of claim 1, wherein detection of the photons uses one of a spatially resolving detector or a spectrally resolving detector.

9. The method of claim 1, wherein the object comprises one or more of inhomogeneous spatial properties, inhomogeneous spectral properties, and a birefringent material.

10. A system, comprising:
a coherent light source adapted to emit a coherent photon beam with a wavelength $\lambda_0$;
a first non-linear medium adapted to generate one or more first correlated photon pairs responsive to the coherent photon beam incident upon the first non-linear medium, each pair comprising two photons with a wavelength $\lambda_1$ and a wavelength $\lambda_2$, respectively, thereby generating a first and a second photon beam with the wavelengths $\lambda_1$ and $\lambda_2$, respectively, wherein the wavelength $\lambda_1$ does not equal the wavelength $\lambda_2$ and the first photon beam is adapted to illuminate an object;
a second non-linear medium adapted to generate one or more second correlated photon pairs responsive to the coherent photon beam and the first photon beam incident upon the second non-linear medium, each pair comprising two photons with the wavelength $\lambda_1$ and the wavelength $\lambda_2$, respectively, thereby generating a third and a fourth photon beam with the wavelengths $\lambda_1$ and $\lambda_2$, respectively;
a dichroic mirror adapted to overlap the photons of wavelength $\lambda_2$ of the first correlated photon pairs with the photons of wavelength $\lambda_2$ of the second correlated photon pairs, such that the overlapped photons of wavelength $\lambda_2$ are indistinguishable; and
an imaging device adapted to detect the overlapped photons of wavelength $\lambda_2$ for imaging the object, such that the photons of wavelength $\lambda_1$ that illuminate the object are not detected.

11. The system of claim 10, wherein the imaging device comprises a CCD camera.

12. The system of claim 10, wherein the imaging device comprises a spectrometer.

13. The system of claim 10, further comprising a dichroic mirror for overlapping the photons of wavelength $\lambda_1$ of the first correlated photon pairs having illuminated the object with the photons of wavelength $\lambda_1$ of the second correlated photon pairs, such that the overlapped photons of wavelength $\lambda_1$ are indistinguishable.

14. The system of claim 10, wherein the first non-linear medium and the second non-linear medium comprise the same physical and optical properties, and the second non-linear medium is spatially separated from the first non-linear medium.

15. The system of claim 10, wherein the first non-linear medium and the second non-linear medium are the same non-linear medium.

16. The system of claim 10, further comprising a mirror adapted for reflecting the photons of wavelength $\lambda_1$ after illuminating the object such as to reverse their optical path.

17. The system of claim 10, wherein the first and second photon beams are generated collinearly and the third and fourth photon beams are generated collinearly.

18. The system of claim 10, wherein each of the generated photon pairs bears spatial and/or spectral correlation.

19. The system of claim 10, wherein the object comprises inhomogeneous spatial and/or spectral properties.

20. The system of claim 10, wherein the object comprises a birefringent material such that the object exhibits birefringence when the object is put under stress.

* * * * *